United States Patent
Seligson et al.

(10) Patent No.: US 9,645,079 B2
(45) Date of Patent: *May 9, 2017

(54) STRUCTURED ILLUMINATION FOR CONTRAST ENHANCEMENT IN OVERLAY METROLOGY

(71) Applicant: KLA-Tencor Corporation, Milpitas, CA (US)

(72) Inventors: Joel Seligson, D.N. Misgav (IL); Noam Sapiens, Bat Yam (IL); Daniel Kandel, Aseret (IL)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/794,294

(22) Filed: Jul. 8, 2015

(65) Prior Publication Data

US 2016/0003735 A1    Jan. 7, 2016

Related U.S. Application Data

(63) Continuation of application No. 13/394,064, filed as application No. PCT/US2012/024320 on Feb. 8, 2012, now Pat. No. 9,104,120.

(Continued)

(51) Int. Cl.
*G01B 11/14* (2006.01)
*G01N 21/47* (2006.01)
(Continued)

(52) U.S. Cl.
CPC ......... *G01N 21/47* (2013.01); *G03F 7/70633* (2013.01); *G01B 11/02* (2013.01); *G01N 21/00* (2013.01)

(58) Field of Classification Search
CPC .... G03F 7/70633; G01N 21/47; G01N 21/00; G01B 11/02
(Continued)

(56) References Cited

U.S. PATENT DOCUMENTS 4,818,110 A    4/1989   Davidson
5,986,740 A    11/1999  Robinson et al.
(Continued)

FOREIGN PATENT DOCUMENTS

WO    WO0227410 A1    4/2002

OTHER PUBLICATIONS

Joel I. Seligson et al., Target noise in overlay metrology. Proc. SPIE 5375, Metrology, Inspection, and Process Control for Microlithography XVIII, 403 (May 24, 2004).
(Continued)

*Primary Examiner* — Tarifur Chowdhury
*Assistant Examiner* — Isiaka Akanbi
(74) *Attorney, Agent, or Firm* — Suiter Swantz pc llo (57) ABSTRACT

Contrast enhancement in a metrology tool may include generating a beam of illumination, directing a portion of the generated beam onto a surface of a spatial light modulator (SLM), directing at least a portion of the generated beam incident on the surface of the SLM through an aperture of an aperture stop and onto one or more target structures of one or more samples, and generating a selected illumination pupil function of the illumination transmitted through the aperture utilizing the SLM in order to establish a contrast level of one or more field images of the one or more target structures above a selected contrast threshold, and performing one or more metrology measurements on the one or more target structures utilizing the selected illumination pupil function.

28 Claims, 8 Drawing Sheets

Related U.S. Application Data (60) Provisional application No. 61/441,540, filed on Feb. 10, 2011, provisional application No. 61/441,553, filed on Feb. 10, 2011.

(51) Int. Cl.
*G03F 7/20* (2006.01)
*G01B 11/02* (2006.01)
*G01N 21/00* (2006.01)

(58) Field of Classification Search
USPC .............. 356/614–620, 445–446, 369, 401
See application file for complete search history.

(56) References Cited

U.S. PATENT DOCUMENTS

| | | | |
|---|---|---|---|
| 6,172,349 B1 | 1/2001 | Katz et al. | |
| 7,339,148 B2 | 3/2008 | Kawano et al. | |
| 7,528,941 B2 | 5/2009 | Kandel et al. | |
| 2004/0066557 A1* | 4/2004 | Anikitchev | G02B 27/1026 359/618 |
| 2005/0068599 A1* | 3/2005 | Mushika | G03F 7/70291 359/237 |
| 2005/0157297 A1 | 7/2005 | Abdulhalim et al. | |
| 2005/0219532 A1 | 10/2005 | Mason | |
| 2009/0141325 A1* | 6/2009 | Sato | G11B 7/0065 359/21 |
| 2010/0060960 A1 | 3/2010 | Tanaka et al. | |
| 2010/0091349 A1 | 4/2010 | Ito et al. | |
| 2010/0182663 A1 | 7/2010 | Yamakawa et al. | |
| 2011/0069312 A1 | 3/2011 | Kandel et al. | |

OTHER PUBLICATIONS

Samson, Edward Carlo et al. Dynamic contrast enhancement in widefield microscopy using projector-generated illumination patterns. New Journal of Physics, vol. 9, Oct. 5, 2007, 15 pages.

Levoy, M. et al. Recording and controlling the 4D light field in a microscope using microlens arrays. 2009, vol. 235, Pt 2, pp. 144-162. Paragraphs 1-3, col. 2 of p. 153, and paragraph 3, col. 2 of p. 154, and Figs. 3-4 and 15.

Neil et al, A wavefront generator for complex pupil function synthesis and point spread function engineering, Journal of Microscopy, vol. 197, Pt 3, Mar. 2000, pp. 319-223.

Neil et al., Optimized pupil-plane filters for confocal microscope point-spread function engineering, Optics Letters, vol. 25, No. 4, Feb. 15, 2000, pp. 245-247.

Bimber et al. Closed-Loop Feedback Illumination for Optical Inverse Tone-Mapping in Light Microscopy. IEEE Transactions on Visulization and Computer Graphics. vol. 17, No. 6, Aug. 5, 2010. Retrieved from the internet: <URL: http://ieeexplore.ieee.org/application/enterprise/entconfirmation.jsp?arnumber=5539757>.

* cited by examiner

STRUCTURED ILLUMINATION FOR CONTRAST ENHANCEMENT IN OVERLAY METROLOGY

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation patent application of United States Non-Provisional Patent Application entitled STRUCTURED ILLUMINATION FOR CONTRAST ENHANCEMENT IN OVERLAY METROLOGY, naming Joel Seligson, Noam Sapiens and Daniel Kandel, as inventors, filed Mar. 2, 2012, Application Ser. No. 13/394,064, which constitutes a national stage of PCT/US2012/24320, filed Feb. 8, 2012, entitled STRUCTURED ILLUMINATION FOR CONTRAST ENHANCEMENT IN OVERLAY METROLOGY, naming Joel Seligson, Noam Sapiens, and Daniel Kandel as inventors, which claims priority to United States Provisional Patent Application entitled STRUCTURED ILLUMINATION FOR CONTRAST ENHANCEMENT IN OVERLAY METROLOGY, naming Joel Seligson, Noam Sapiens and Daniel Kandel, as inventors, filed Feb. 10, 2011, Application Ser. No. 61/441,540, and United States Provisional Patent Application entitled STRUCTURED ILLUMINATION FOR CONTRAST ENHANCEMENT IN OVERLAY METROLOGY, naming Joel Seligson, Noam Sapiens and Daniel Kandel as inventors, filed Feb. 10, 2011, Application Ser. No. 61/441,553. U.S. Non-Provisional patent application Ser. No. 13/394,064; PCT Patent Application No. PCT/US2012/24320; U.S. Provisional Patent Application Ser. No. 61/441,540; and U.S. Provisional Patent Application Ser. No. 61/441,553 are each incorporated herein by reference in their entirety.

TECHNICAL FIELD

The present invention generally relates to overlay metrology, and more particularly to a system for enhancing target contrast in an overlay metrology system.

BACKGROUND

In a variety of manufacturing and production settings, there is a need to control alignment between various layers or within particular layers of a given sample. For example, in the context of semiconductor processing, semiconductor-based devices may be produced by fabricating a series of layers on a substrate, some or all of the layers including various structures. The relative position of these structures both within a single layer and with respect to structures in other layers is critical to the performance of the devices. The misalignment between various structures is known as overlay error.

Figure 1:
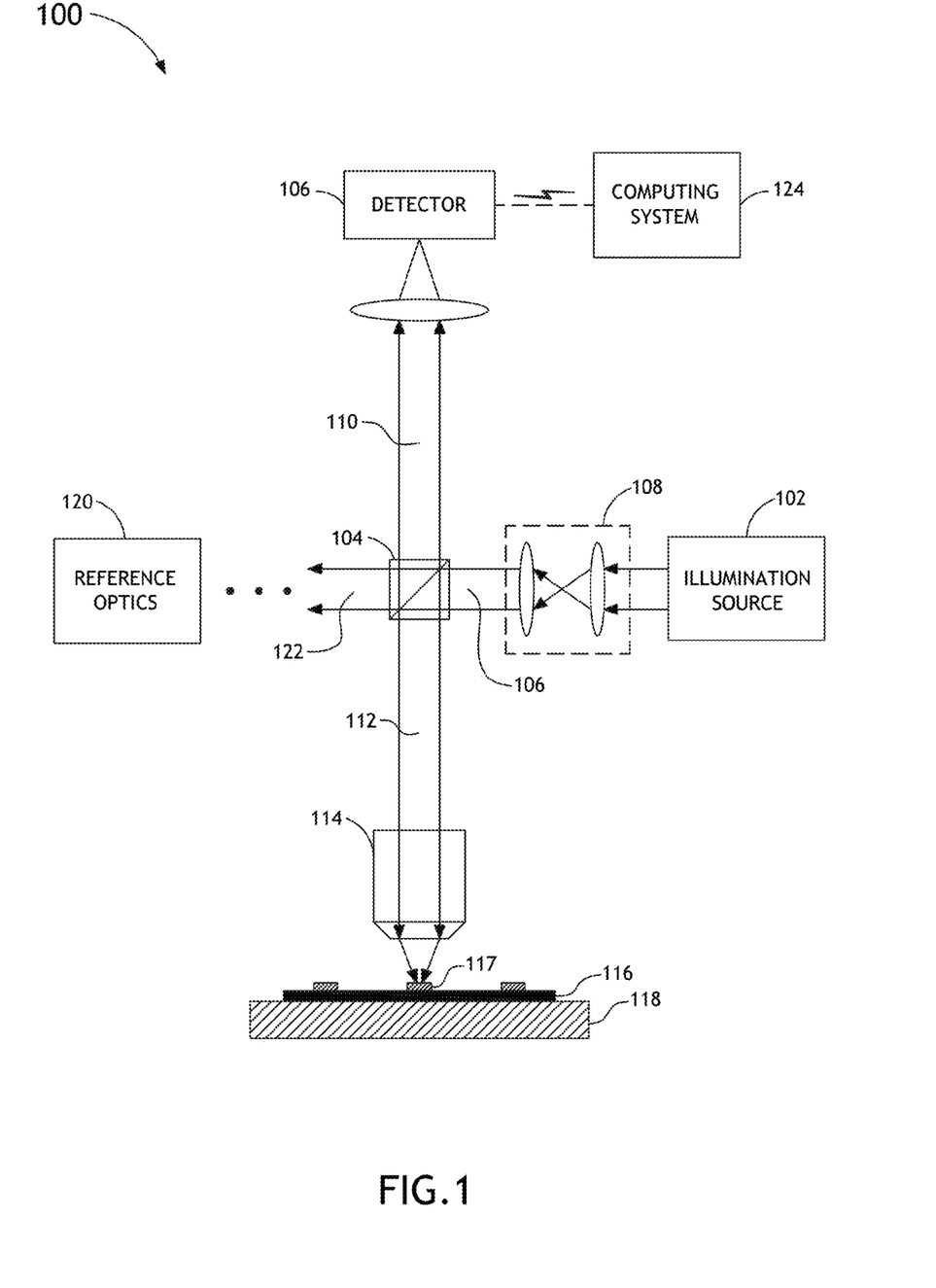
FIG. 1 is a schematic view of a conventional overlay metrology measurement system.

Conventional overlay metrology systems, such as imaging or scatterometry based systems, are typically based on bright field illumination microscopy in which a dedicated metrology target, containing spatial information from at least two separate process steps is imaged onto a two dimensional sensor array. FIG. 1 illustrates a conventional overlay metrology system 100. The system 100 may include an illumination source 102 (e.g., broadband or narrowband source), a set of illumination optics 108, a beam splitter 104 configured to direct a light beam 112 to an objective 114, which in turn focuses the light onto one or more targets 117 of the wafer 116 disposed on a sample stage 118. The light is then scattered from a metrology target 117 of the wafer 116 and is transmitted along the imaging path 110 onto an imaging plane of the detector 106. Some metrology systems consist of a two beam (e.g., illumination path and reference path) interferometric configuration. Conventional two-beam metrology systems include a set of reference optics 120, which include, but are not limited to, a reference mirror, a reference objective, and a shutter configured to selectively block the reference path 122. In a general sense, a two-beam interference optical system may be configured as a Linnik interferometer. Linnik interferometry is described generally in U.S. Pat. No. 4,818,110, issued on Apr. 4, 1989, and U.S. Pat. No. 6,172,349, issued on Jan. 9, 2001, which are incorporated herein by reference.

The measurement of overlay error between successive patterned layers on a wafer is one of the most critical process control techniques used in the manufacturing of integrated circuits and devices. Overlay accuracy generally pertains to the determination of how accurately a first patterned layer aligns with respect to a second patterned layer disposed above or below it and to the determination of how accurately a first pattern aligns with respect to a second pattern disposed on the same layer. Presently, overlay measurements are performed via test patterns that are printed together with layers of the wafer. The images of these test patterns are captured via an imaging tool and an analysis algorithm is used to calculate (e.g., calculated using a computing system 124 coupled to an output of the detector 106) the relative displacement of the patterns from the captured images. Such overlay metrology targets (or 'marks') generally comprise features formed in two layers, the features configured to enable measurement of spatial displacement between features of the layers (i.e., the overlay or displacement between layers).

Overlay measurement precision, however, is limited by the level of achievable contrast in a given metrology system. Contrast in an optical metrology system is generally constrained by the peak to valley difference in the image projection of the lowest contrast target feature. Further, metrology accuracy and tool induced shift (TIS) performance is limited by contrast, also generally constrained by the peak to valley difference in the image projection of the lowest contrast target feature. In many metrology target architectures, a contrast reversal of an edge or periodic feature may occur when illuminated from different angles of incidence (i.e., illuminated from different locations in the illumination pupil). When a target is simultaneously illuminated from multiple angles of incidence the effect of contrast reversal may act to reduce or even eliminate the observed contrast entirely when light from multiple angles of incidence are integrated in the image plane.

Conventional optical metrology systems control contrast utilizing fixed apertures and the lateral movements of fixed apertures (e.g., using piezoelectric control). The conventional systems are limited, in part, because of their binary nature (i.e., ON or OFF). Although existing targets and target measurement systems are suitable for many implementation contexts, it is contemplated herein that many improvements may be made. The invention described herein discloses methods and apparatuses which overcome the disadvantages of the prior art.

SUMMARY

An apparatus suitable for contrast enhancement in a metrology tool is disclosed. In one aspect, the apparatus suitable for contrast enhancement in a metrology tool may include, but is not limited to, an illumination source; a spatial light modulator (SLM); a beam splitter configured to direct a portion of light emanating from the illumination source along an illumination path to a surface of the spatial light modulator (SLM); an aperture stop disposed substantially at a pupil plane of the illumination path, the aperture stop having an aperture configured to transmit at least a portion of light directed from the surface of the SLM to a surface of one or more specimens; and a metrology tool configured to measure one or more characteristics of one or more metrology target structures of the one or more specimens, the metrology tool comprising: an entrance pupil configured to receive illumination directed from the surface of the SLM and transmitted through the aperture of the aperture stop; a beam splitter configured to receive illumination received through the entrance pupil of the metrology tool, the beam splitter further configured to direct at least a portion of the illumination passed through the entrance pupil to the one or more samples; an objective lens configured to focus the at least a portion of the illumination onto one or more target structures of the one or more samples; and a detector configured to collect a portion of illumination scattered from the one or more target structures of the one or more samples, wherein the SLM is configured to control a contrast level of the metrology tool by controlling an illumination pupil function of the illumination transmitted through the aperture, the illumination pupil function controlled by controlling a profile of illumination impinging on the surface of the SLM from the illumination source.

In another aspect, the apparatus suitable for contrast enhancement in a metrology tool may include, but is not limited to, a laser light source configured to generate one or more laser beams; an integration rod optically coupled to an output of the laser source; a micro mirror array (MMA) chip; a beam splitter configured to direct a portion of light emanating from the integration rod along an optical path toward a surface of the MMA chip; a set of optical relay optics configured to receive the directed portion of light from the beam splitter and relay the portion of light to the MMA chip; a metrology tool configured to measure one or more characteristics of one or more metrology target structures of one or more samples, the metrology tool comprising: an entrance pupil configured to receive illumination directed from the surface of the MMA chip; a beam splitter configured to receive illumination received through the entrance pupil of the metrology tool, the beam splitter further configured to direct at least a portion of the illumination passed through the entrance pupil to the one or more samples; an objective lens configured to focus the at least a portion of the illumination onto one or more target structures of the one or more samples; and a detector configured to collect a portion of illumination scattered from the one or more target structures of the one or more samples, a removable lens positioned along an imaging path of the metrology tool and configured to alternate the detector between imaging the one or more samples and a pupil of the objective, the MMA chip being imaged to the pupil of the objective, wherein the MMA chip is configured to control a contrast level of the metrology tool by controlling a profile of illumination impinging on the surface of the MMA chip from the laser source.

A method for contrast enhancement in a metrology tool is disclosed. In one aspect, method for contrast enhancement in a metrology tool may include, but is not limited to, generating a beam of illumination; directing a portion of the generated beam onto a surface of a spatial light modulator (SLM); directing at least a portion of the generated beam incident on the surface of the SLM through an aperture of an aperture stop and onto one or more target structures of one or more samples; generating a selected illumination pupil function of the illumination transmitted through the aperture utilizing the SLM in order to establish a contrast level of one or more field images of the one or more target structures above a selected contrast threshold; and performing one or more metrology measurements on the one or more target structures utilizing the selected illumination pupil function.

A method for contrast enhancement in a metrology tool is disclosed. In one aspect, method for contrast enhancement in a metrology tool may include, but is not limited to, generating a beam of illumination; directing a portion of the generated beam onto a surface of a spatial light modulator; directing at least a portion of the generated beam incident on the surface of the spatial light modulator through an aperture of an aperture stop and onto one or more target structures of one or more samples; and acquiring a plurality of field images of the one or more target structures of one or more samples utilizing a detector of a metrology tool, each field image being acquired at a different illumination pupil function, wherein each of the different illumination pupil functions is achieved utilizing the spatial light modulator; calculating a plurality of contrast levels by determining a contrast level for each of the plurality of field images of the one or more target structures; identifying a measurement illumination pupil function, wherein the measurement illumination pupil function corresponds to the largest of the plurality of contrast levels; and performing one or more metrology measurements utilizing the identified measurement illumination pupil function.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Reference will now be made in detail to the subject matter disclosed, which is illustrated in the accompanying drawings.

Referring generally to FIGS. 2A through 4, the systems 200 and 400 suitable for providing contrast enhancement of an overlay metrology target measured with a metrology tool are described in accordance with the present invention. One limitation associated with state of the art overlay metrology targets includes the potential for lack of information content (i.e., contrast level) associated with the small measurement structures of the targets. The systems 200 and 400 are directed at providing enhanced contrast levels to counteract the presence of low contrast in one or more target structures. In a general sense, contrast in a target image is a strong function of the illumination pupil structure of the light utilized to analyze the given target (e.g., BiB target or AIM target). Systems 200 and 400 are directed at the utilization of structured illumination controlled by a spatial light modulator positioned within the illumination path of an implementing metrology tool in order to enhance the contrast level associated with one or more measurement structures of one or more overlay targets of one or more wafer samples.

It is noted herein that throughout the present disclosure the terms "wafer" and "samples" are used interchangeably. As used throughout the present disclosure, the terms "wafer" and "sample" generally refer to a substrate formed of a semiconductor or non-semiconductor material. For example, a semiconductor or non-semiconductor material may include, but is not limited to, monocrystalline silicon, gallium arsenide, and indium phosphide. A wafer may include one or more layers. For instance, such layers may include, but are not limited to, a resist, a dielectric material, a conductive material, and a semiconductive material. Many different types of such layers are known in the art, and the term wafer as used herein is intended to encompass a wafer on which all types of such layers may be formed. A typical semiconductor process includes wafer processing by lot. As used herein a "lot" is a group of wafers (e.g., group of 25 wafers) which are processed together. Each wafer in the lot is comprised of many exposure fields from the lithography processing tools (e.g. steppers, scanners, etc.). Within each field may exist multiple die. A die is the functional unit which eventually becomes a single chip. On product wafers, overlay metrology targets are typically placed in the scribeline area (for example in the 4 corners of the field). This is a region that is typically free of circuitry around the perimeter of the exposure field (and outside the die). In some instances, overlay targets are placed in the streets, which are regions between the die but not at the perimeter of the field. It is fairly rare for overlay targets to be placed on product wafers within the prime die areas, as this area is critically needed for circuitry.

One or more layers formed on a wafer may be patterned or unpatterned. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated Referring now to FIGS. 2A through 2B, the system 200 suitable for providing contrast enhancement of an overlay metrology measured with an metrology tool is described in accordance with the present invention. The system 200 suitable for contrast enhancement of an overlay metrology target may include an illumination source 202, a beam splitter 208, a spatial light modulator (SLM) 206, an aperture stop 218 having an aperture 219, and an overlay metrology tool 224 configured to measure one or more metrology characteristics (e.g., overlay error) of one or more overlay targets 229 of the one or more wafers 230 disposed on a sample stage 232. In a further aspect, the system 200 may include a first Fourier lens 216 and a second Fourier lens 220.

Figure 2A:
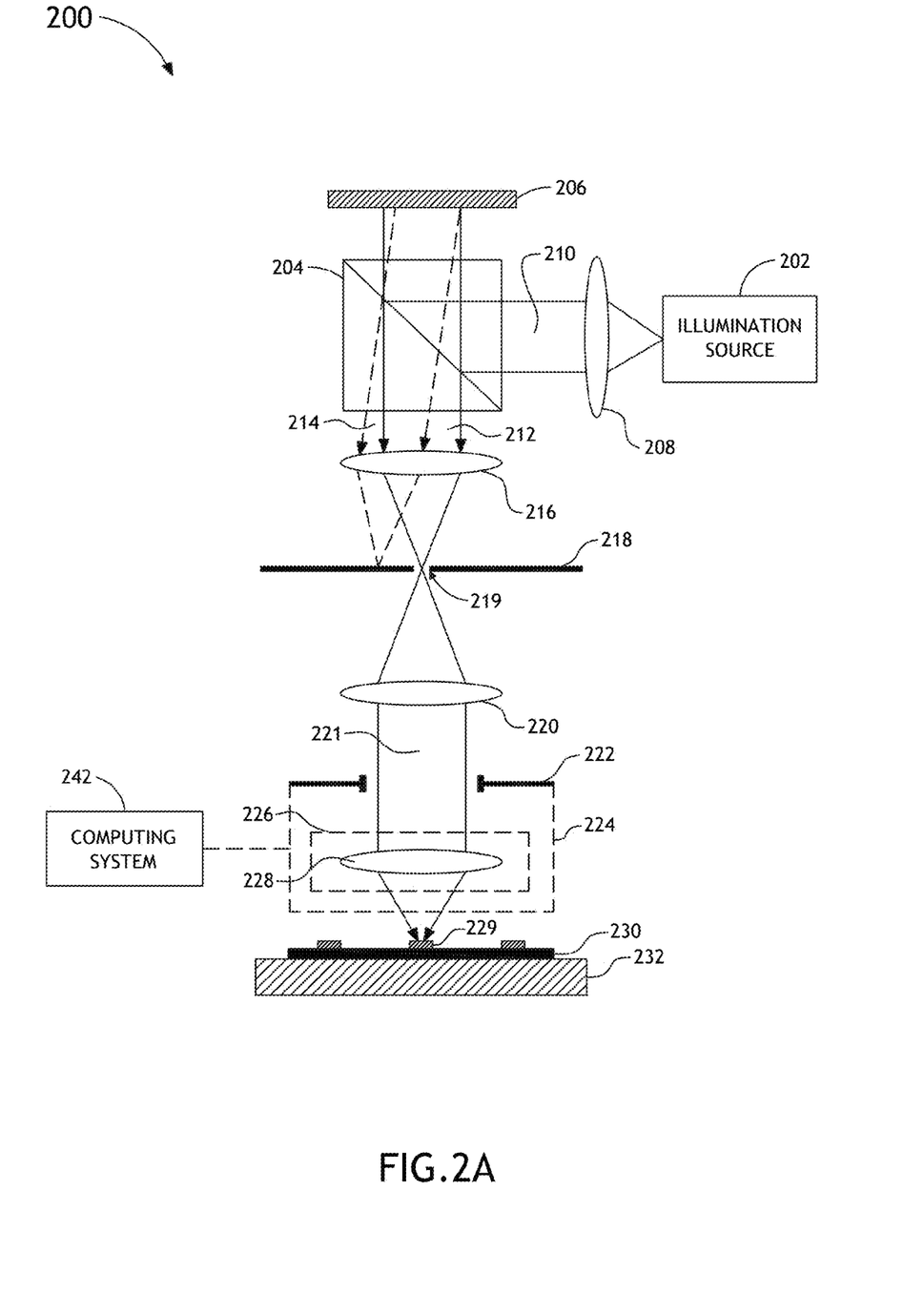
FIG. 2A is a schematic view of a system suitable for contrast enhancement in a metrology tool, in accordance with one embodiment of the present invention.

In one aspect of the invention, the SLM 206 is configured to control a contrast level of the metrology tool 224. In this regard, the SLM 206 of the system 200 controls the contrast of one or more field images obtained using the metrology tool 224 by controlling the illumination pupil function of the illumination passing through the aperture 219 of the system 200. It is noted herein that the introduction of a SLM 206 into the illumination path 210 of a metrology system provides for the full spatial control of the illumination pupil structure of the illumination, thereby allowing the system 200 to control the contrast level of the lowest contrast feature of an examined metrology target 229 of the one or more wafers 230. In this regard, the SLM 206 of the system 200 may act to control the illumination pupil function (and thereby target contrast) by controlling the profile of illumination impinging on the surface of the SLM from the illumination source 202. For example, as shown in FIG. 2A, the SLM 206 may be configured to selectably produce a first illumination configuration 212 and a second illumination configuration 214.

In one embodiment, the SLM 206 of the present invention may include, but is not limited to, a micro electro-mechanical system (MEMS) based SLM device. For example, the SLM 206 may include a diffraction-based SLM, such as, but not limited to, a micro mirror array (MMA) chip, as discussed further herein. By way of another example, the SLM 206 may include a reflection-based SLM. In another embodiment, the SLM 206 of the present invention includes a liquid crystal based SLM.

Figure 3A:
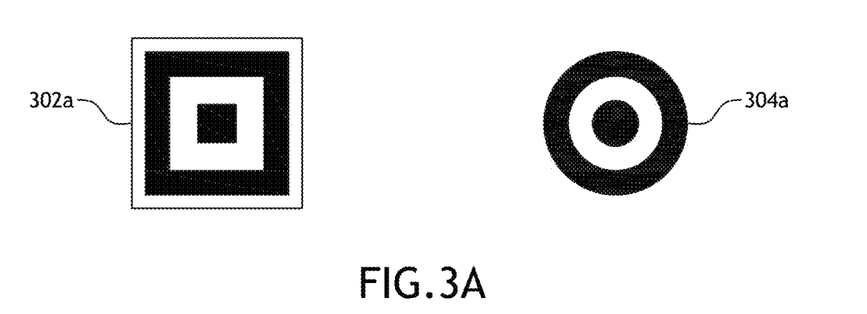
FIG. 3A is a conceptual view of a field image of an overlay target and a corresponding illumination pupil image, in accordance with one embodiment of the present invention.
Figure 3B:
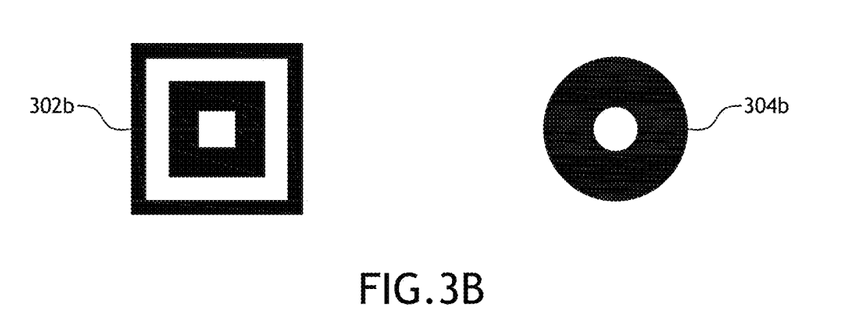
FIG. 3B is a conceptual view of a field image of an overlay target and a corresponding illumination pupil image, in accordance with one embodiment of the present invention.
Figure 3C:
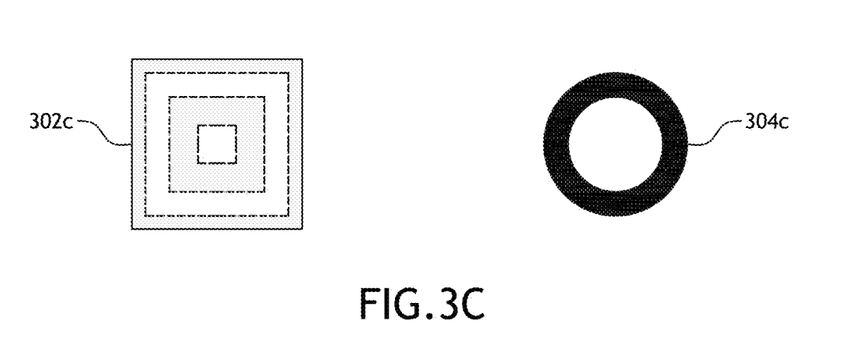
FIG. 3C is a conceptual view of a field image of an overlay target and a corresponding illumination pupil image, in accordance with one embodiment of the present invention.

Referring now to FIG. 3A through 3C, a series of illumination pupil images (e.g., 304a, 304b, and 304c) and their corresponding field images (e.g., 302a, 302b, and 302c) are illustrated. It is noted herein that the "white portion" of the illumination pupil images corresponds to the angles of illumination. It is further recognized herein that illumination incident on a target 229 having a specific range of incidence angles may generate a field image having an edge function that increases at the traversal from an inner edge outward, while a different range of incidence angles may generate a field image having an edge function that decreases at the traversal from an inner edge outwards. The combination of these two configurations may create an image having increased signal strength, but with diminished contrast, as illustrated in FIG. 3C, which in turn may negatively impact metrology performance.

For the specific set of conditions associated with the acquisition of field images of the targets 302*a*, 302*b*, and 302*c*, Applicants have found that an annular illumination field 304*a* produced the highest contrast field image, as illustrated in FIG. 3A. It is noted herein that the ultimate preferred illumination field may depend on a variety of factors. These factors include, but are not limited to, specific features, topography, and stack parameters. As such, the illumination pupil fields (e.g., 304*a*, 304*b*, and 304*c*) and their corresponding field images (e.g., 302*a*, 302*b*, and 302*c*) should not be interpreted as limitations on the present invention, but merely illustrative in nature.

It is noted that the SLM 206 may achieve multiple illumination pupil functions, such as those depicted in FIGS. 3A-3C, by adjusting the illumination profile of the illumination impinging on the surface of the SLM 206 from the illumination source 202. This capability allows the system 200 (or system 400 described further herein) to be trained by monitoring contrast of one or more field images of one or more overlay targets 229 as a function of illumination pupil image. Once an optimized or nearly optimized illumination pupil function has been achieved the system 200 (via user selection or via computing system 242 control) may perform overlay metrology measurements using the optimized illumination pupil function. The training and measurement processes associated with optimizing the contrast of the target images obtained using the system 200 (or system 400) are discussed in greater detail further herein.

The illumination source 202 of the system 200 may include any illumination source known in the art. In one embodiment, the illumination source 202 may include a narrowband light source. It should be recognized that any known narrowband light source is suitable for implementation in the present invention. For example, in a preferred embodiment, the illumination source 202 may include, but is not limited to, one or more laser light sources. For instance, the illumination source 202 may include, but is not limited to, a diode-pumped solid state (DPSS) laser (e.g., 532 nm DPSS Nd: YAG CW laser). In one embodiment, the illumination source 202 may include a broadband light source (e.g., white light source). For example, the illumination source 202 may include, but is not limited to, a halogen light source (HLS). For instance, the halogen light source may include, but is not limited to, a tungsten based halogen lamp. In another example, the illumination source 202 may include a Xenon arc lamp. It is recognized herein that when implementing a broadband source a reflection-based SLM may be utilized in conjunction with a broadband source. In another instance, it is recognized that the spectrum of the output of a given broadband source may be narrowed. For example, the output of a broadband source may be narrowed to approximately 10 nm. Those skilled in the art should recognize that there exist a variety of settings wherein a broadband source may be utilizing in the context of the present invention. As such, the description provided above should not be interpreted as limiting but merely as an illustration.

In another aspect of the invention, the beam splitter 204 is configured to direct a portion of light emanating from the illumination source 202 toward the surface of the SLM 206. In this regard, the beam splitter 204 may split the light beam emanating from an illumination source 202 into two beams such that at least one of the beams is directed toward the surface of the SLM 206. The beam splitter 204 is further configured to allow for the transmission of illumination emanating from the surface of the SLM 206 toward the one or more wafers 230 via the aperture 219. It is contemplated herein that any beam splitting technology known in the art is suitable for implementation in the present invention.

In another aspect of the invention, the aperture stop 218 is disposed at a pupil plane of the illumination path 212. In this manner, the aperture stop 218 is arranged such that the aperture 219 of the aperture stop 218 is positioned to transmit a portion of the light directed from the surface of the SLM 206 and through the beam splitter 204 to a surface of the one or more wafers 230.

In another aspect of the present invention, the first Fourier lens 216 may be positioned between the SLM 206 and the aperture 219, while a second Fourier lens 220 may be positioned between the aperture 219 and an entrance pupil 222 of the metrology optics 226 (e.g., objective lens 228, imaging optics 238, and the like) of the metrology tool 224. In a further embodiment, the first Fourier lens 216 may be configured to perform a Fourier transform on illumination 212 received from the SLM. Further, the second Fourier lens 220 may perform an inverse Fourier transform on illumination passed through the aperture 219. In this regard, the aperture 219 of aperture stop 218 may be configured as a Fourier aperture. The second Fourier lens 220 may further be configured to direct illumination 221 toward the entrance pupil 222 of the metrology optics 226 of the metrology tool 224.

Figure 2B:
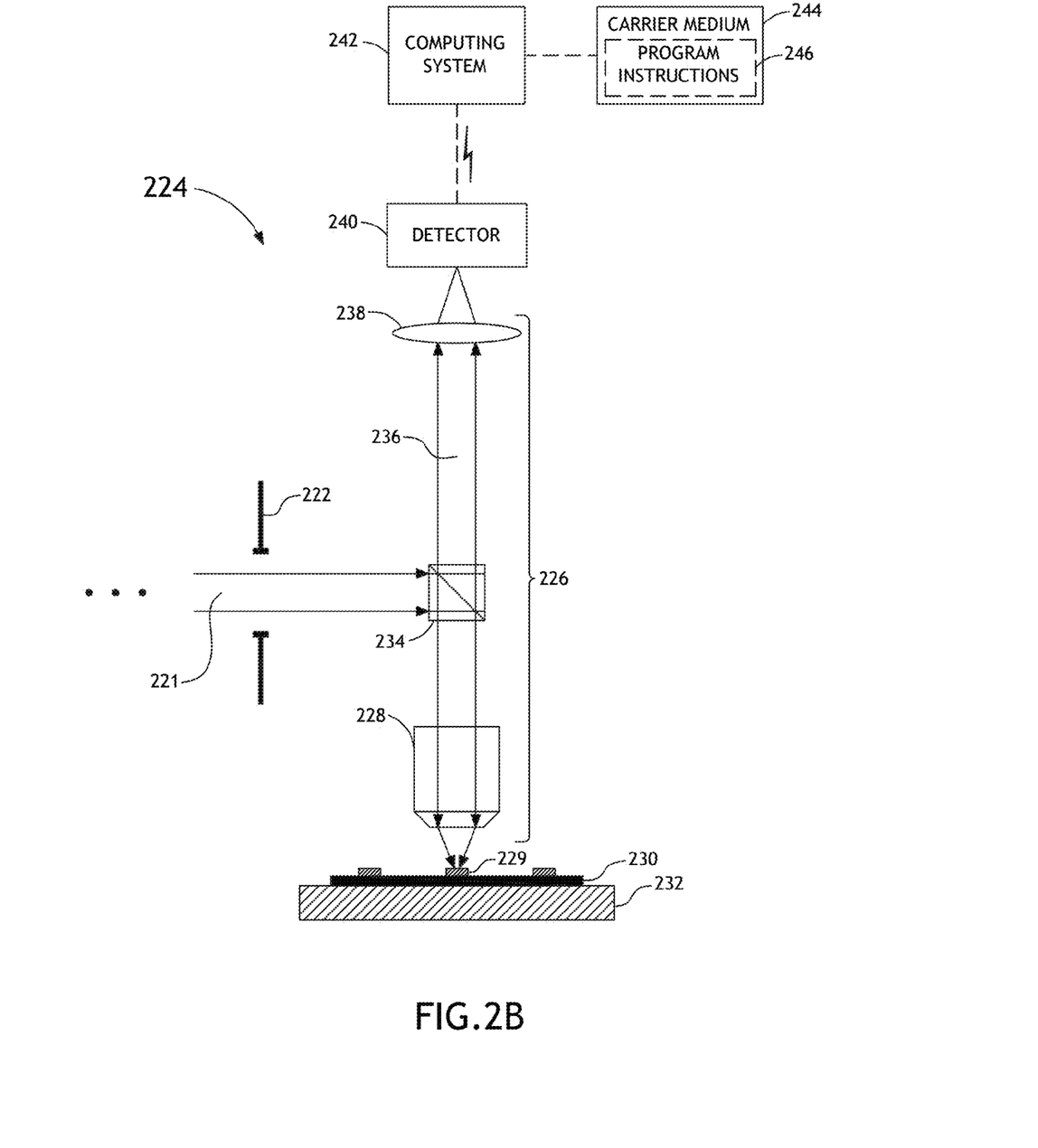
FIG. 2B is a schematic view of a metrology tool of a system suitable for contrast enhancement in a metrology tool, in accordance with one embodiment of the present invention.

In one aspect of the present invention, as shown in FIG. 2B, the metrology tool 224 of the system 200 may include an entrance pupil 222, a set of metrology optics 226, and a detector 240. In a further aspect, the entrance pupil 222 of the metrology tool 224 is configured to receive illumination directed from the SLM 206 and passed through the aperture 219. In this manner, the entrance pupil 222 acts as an entrance pupil to the metrology optics 226 (e.g., objective 228, imaging optics 238, beam splitter 234 and the like) of the metrology tool 224.

In another aspect, the metrology optics 226 of the metrology tool 224 may include an objective lens 228. The objective lens 228 may aid in directing light along the object path 235 of the metrology tool 224 to the surface of the wafer 230 disposed on the sample stage 232. For example, the beam splitter 234 may direct a portion of the light beam 221 entering the metrology optics 226 via the entrance pupil 222 along the object path 235. Following the splitting process by the beam splitter 234, the objective lens 228 may focus light from the object path 235 onto one or more overlay targets 229 of the wafer 230. In a general sense, any objective lens known in the art may be suitable for implementation as the objective lens 228 of the metrology tool 224 of the present invention.

Further, a portion of the light impinging on the surface of the wafer 230 may be scattered by the one or more overlay targets 229 of the wafer 230 and directed along the optical axis via the objective 228, the beam splitter 234, and imaging optics 238 toward the detector 240. It should be further recognized that intermediate optics devices such as intermediate lenses, additional beam splitters (e.g., a beam splitter configured to split off a portion of light to a focusing system), and additional imaging lenses may be placed between the objective 228 and the imaging plane of the detector 240.

In another aspect, the detector 240 of the metrology tool 224 may be disposed along an optical axis of the metrology tool 224, the optical axis being at least substantially arranged perpendicular to the surface of the wafer 230. In this regard, the detector 240 may be arranged to collect imagery data from the surface of the wafer 230. For example, in a general sense, after scattering from at least the one or more targets 229 of the wafer 230, light may travel along the optical axis to the image plane of the detector 240 via the objective 228, the beam splitter 234 and the imaging lens 238. It is recognized that any detector system known in the art is suitable for implementation in the present invention. For example, the detector 240 may include a charge coupled device (CCD) based camera system. By way of another example, the detector 240 may include a time delay integration (TDI)-CCD based camera system.

While the above description describes the detector 240 as being located along an optical axis oriented perpendicular to the surface of the wafer 230, this characteristic should not be interpreted as a requirement. It is contemplated herein that the detector 240 may be situated along an additional optical axis of the system 200. For example, in a general sense, one or more additional beam splitters may be utilized to divert a portion of light reflected from the surface of the wafer 230 and traveling along the object path 235 onto an additional optical axis. The detector 240 may be arranged such that light traveling along the additional optical axis impinges the image plane of the detector 240.

It is contemplated herein that the systems 200 and 400 of the present invention may consist (but are not required to consist) of adapting or reconfiguring presently existing optical metrology systems. For instance, the present invention may consist of adapting the KLA-Tencor Archer 100 or 200 overlay control systems. For example, in the case of system 200, a SLM 206, beam splitter 204, aperture stop 218 and Fourier lenses 218 and 220 may be arranged to process light emanating from an illumination source 202. Further, the illumination source of the preexisting metrology system (e.g., KLA-Tencor Archer 100 or 200) may be removed and replaced with an entrance pupil 222 configured to receive illumination 221 processed by the components described herein. It should be recognized that the present invention is not limited to an adaptation of an Archer 100 or 200 systems, but rather the description above should be interpreted merely as an illustration. It is anticipated that the present invention may be extended to a wide variety of microscopy and overlay metrology systems.

Figure 2C:
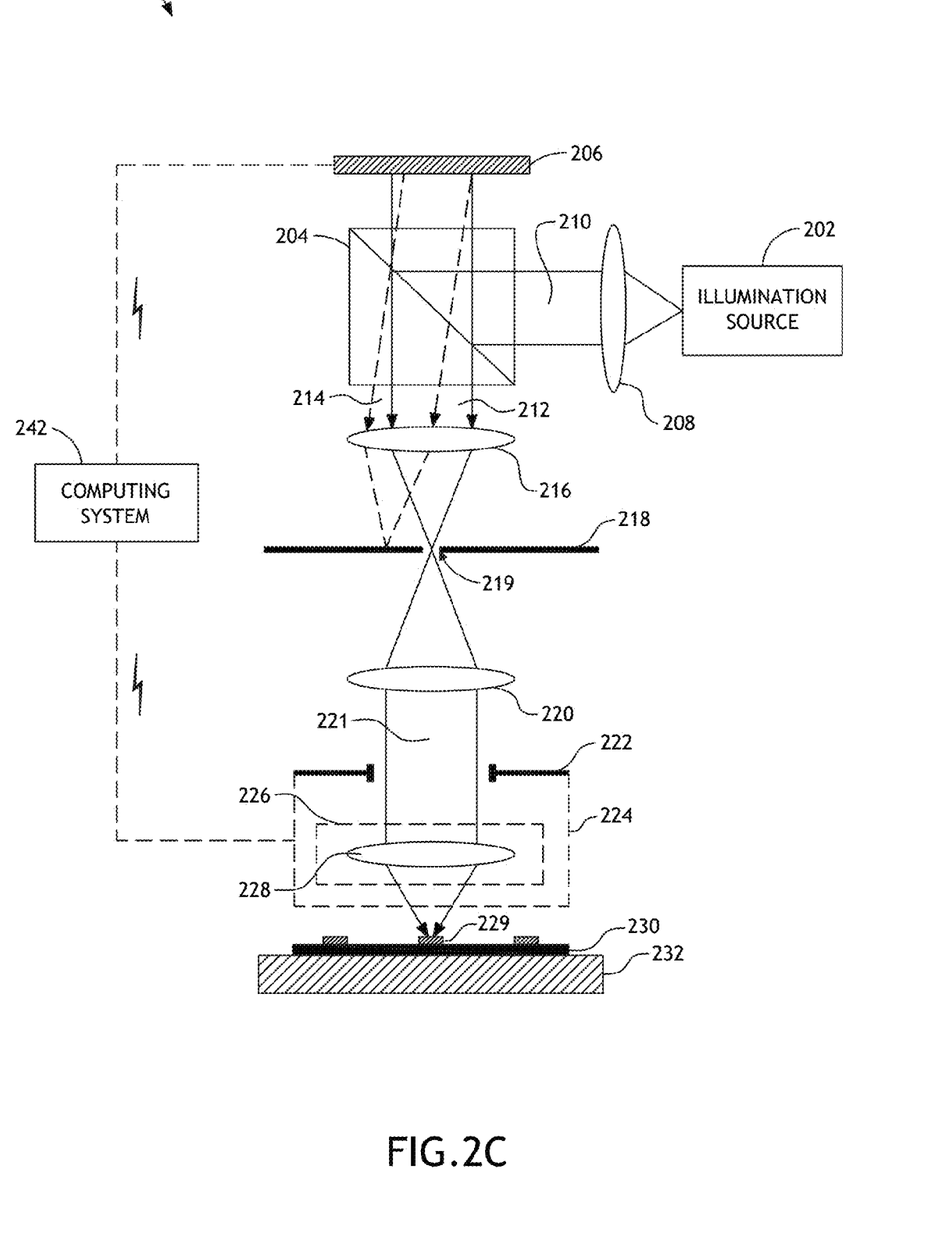
FIG. 2C is a schematic view of a system suitable for contrast enhancement in a metrology tool, in accordance with one embodiment of the present invention.

In another aspect of the present invention, as shown in FIGS. 2A-2C, the system 200 may include one or more computing systems 242 communicatively coupled to the detector 240 of the metrology tool 224 and configured to determine one or more overlay characteristics (e.g., overlay error) utilizing the illumination collection data provided by the output of the detector 240. As such, the one or more computing systems 242 may be configured to receive a set of measurements performed by the metrology tool 224 in a sampling process of one or more wafers 230 of a lot. In this regard, digitized imagery data may be transmitted from the detector 240 to the one or more computing systems 242 via a signal, such as a wireline signal (e.g., copper line, fiber optic cable, and the like) or a wireless signal (e.g., wireless RF signal). Upon receiving results of the one or more sampling process from the metrology tool 224, the one or more computer systems 242 may then calculate one or more overlay values associated with the sampled overlay targets via a preprogrammed overlay determination algorithm (stored as a portion of the program instructions 246 stored on the carrier medium 244).

In an alternative embodiment, shown in FIG. 2C, the one or more computing systems 242 may be communicatively coupled to both the detector 240 of the metrology system 224 and the SLM 206. In one aspect, the one or more computing systems 242 may be configured to receive a plurality of field images of the sampled overlay targets 229 of the wafer 230 from the detector 240. In a further aspect, each of the field images may be acquired at a different illumination pupil function, wherein each of the illumination pupil functions is established utilizing the SLM 206, as described previously herein. In another aspect, the one or more computing systems 242 may calculate a contrast level for each of the acquired field images utilizing illumination collection data received from the detector 240 along with one or more contrast metrics. The use of contrast metrics to calculate contrast in images of overlay targets is described generally in Seligson et. al, "Target Noise in Overlay Metrology," Metrology, Inspection, and Process Control for Microlithography XVIII, edited by Richard M. Silver, Proceedings of SPIE Vol. 5375 (2004), which is incorporated herein by reference. In an additional aspect, the one or more computing systems 242 may determine an illumination function suitable for producing a desired contrast level (e.g., a contrast level above a selected contrast threshold or an optimal contrast level of the system/targets) utilizing the calculated contrast levels for each of the acquired field images. In response to the this determination of the suitable illumination function, the one or more computing systems 242 may control the SLM 206 in order to establish an SLM 206 configuration that produces the suitable illumination function thereby producing an a field image contrast level at or above the desire contrast level.

In a further embodiment, the metrology tool 224 may be configured to accept instructions from the one or more computing systems 242 of the system 200. Upon receiving instructions from the computing system 242, the metrology tool 242 may perform one or more overlay metrology measurements. In this regard, upon achieving the desired contrast level by controlling the SLM 206 to establish a selected illumination function, the one or more computing systems 242 may direct the metrology tool 242 to carry out one or more metrology measurements. In a further embodiment, the metrology tool 242 may perform overlay metrology at various locations of the wafer 230 identified in the instructions provided by the one or more computing systems 242.

It should be recognized that the various steps described throughout the present disclosure may be carried out by a single computer system or, alternatively, a multiple computer system. Moreover, different subsystems of the system 200, such as the metrology tool 224, may include a computer system suitable for carrying out at least a portion of the steps described above. Therefore, the above description should not be interpreted as a limitation on the present invention but merely an illustration. Further, the one or more computing systems 242 may be configured to perform any other step(s) of any of the method embodiments described herein.

In another embodiment, the one or more computing systems 242 may be communicatively coupled to the detector 240 of the metrology tool 224 and/or the SLM 206 in any manner known in the art. For example, the one or more computing systems 242 may be coupled to a computer system of the metrology tool 224 or to a computer system of a programmable SLM 206. In another example, the metrology tool 224 and the SLM 206 may be controlled by a single computer system. Moreover, the one or more computing systems 242 of the system 200 may be configured to receive and/or acquire data or information from other systems (e.g., inspection results from an inspection system, metrology results from an additional metrology system, or process tool correctables calculated from a system, such as KLA-Tencor's KT Analyzer) by a transmission medium that may include wireline and/or wireless portions. In this manner, the transmission medium may serve as a data link between the one or more computing systems 242 and other subsystems of the system 200. Moreover, the one or more computing systems 242 may send data to external systems via a transmission medium.

The one or more computing systems 242 may include, but are not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 246 implementing methods such as those described herein may be transmitted over or stored on carrier medium 244. The carrier medium may be a transmission medium such as a wire, cable, or wireless transmission link. The carrier medium may also include a permanent storage medium such as a read-only memory, a random access memory, a magnetic or optical disk, or a magnetic tape.

Figure 4:
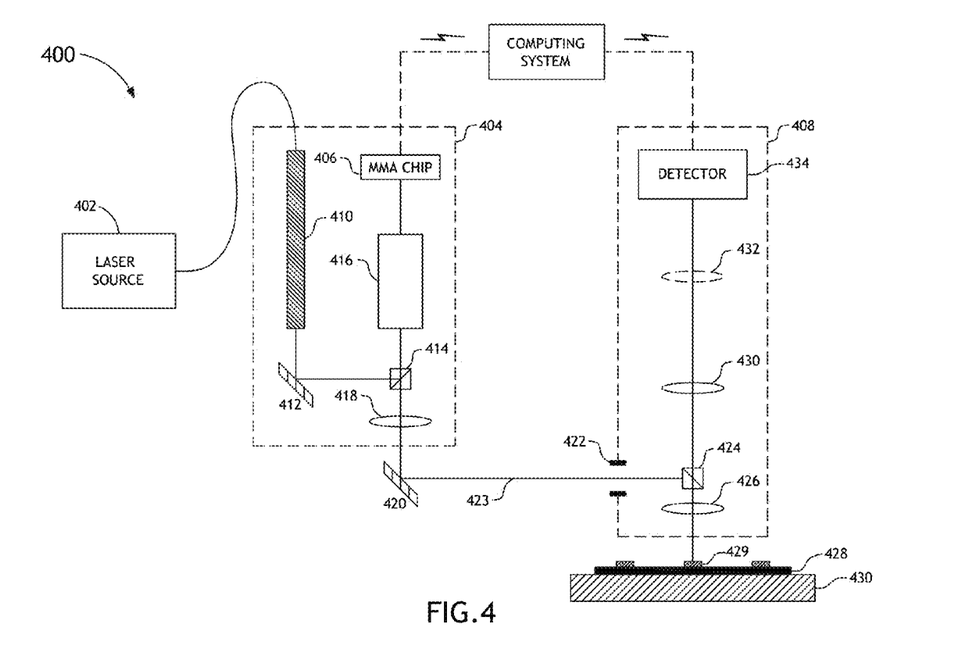
FIG. 4 is a schematic view of a system suitable for contrast enhancement in a metrology tool, in accordance with a preferred embodiment of the present invention.

Referring now to FIG. 4, a preferred embodiment of the present invention is shown. The applicant notes that unless otherwise noted the description relating to the system 200 of FIGS. 2A-2C should be interpreted to apply to system 400 of FIG. 4. In one aspect, the system 400 includes a laser light source 402 configured to generate one or more laser beams, an integration rod 410 optically coupled to the laser light source 402, and a micro mirror array (MMA) chip 406. In a further aspect, the system 400 includes a beam splitter 414 configured to receive illumination from the integration rod 410 and direct the illumination toward the MMA chip 406. It is noted herein that the components described above may act to from a micro mirror imaging device 404.

In a further embodiment, the micro mirror imaging device 404 may further include a steering mirror 412 in order to assist in optically coupling the output of the integration rod 410 and the MMA chip. In addition the micro mirror imaging device 404 may further include a set of Schlieren optics 416 positioned between the beam splitter 414 and the MMA chip 406 and configured to process the laser illumination transmitted from the laser source 402 and through the beam splitter 414. Further, the micro imaging device 404 may include an exit lens 418.

In another aspect, the system 400 includes a metrology tool 408. As in system 200, the metrology tool 408 of system 400 includes, but is not limited to, a detector 434, an objective 426, a beam splitter 424, and imaging optics 430. In one aspect, the micro mirror device 404 and the metrology tool 408 are optically coupled via beam 423 passing through the entrance pupil 422 of the metrology optics of the metrology tool 408. In a further aspect, the metrology tool 408 includes a removable mirror 432 positioned along an imaging path of the metrology tool 408. It is noted herein that the removable lens 432 may be implemented in order to alternate the detector 434 between imaging the one or more samples 428 and a pupil of the objective 426. It is further noted herein that the MMA chip is imaged to the objective 426. As such, imaging the objective 426 is equivalent to imaging the MMA chip 406.

The embodiments of systems 200 and 400 illustrated in FIGS. 2A-2C, 3A-3C, and 4 may be further configured as described herein. In addition, the system 200 may be configured to perform any other step(s) of any of the method embodiment(s) described herein.

Figure 5:
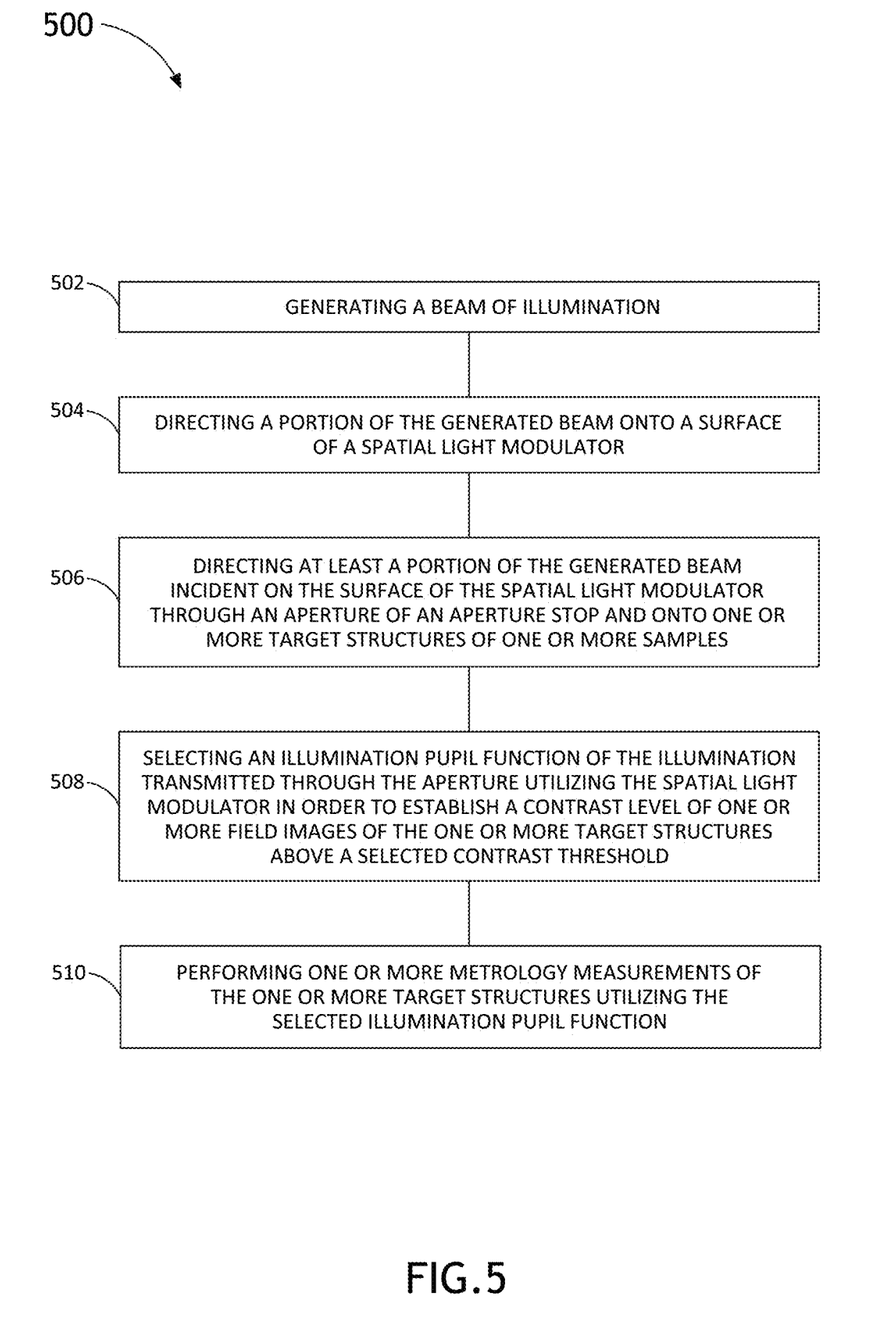
FIG. 5 is a process flow diagram of a method for contrast enhancement in a metrology tool, in accordance with one embodiment of the present invention.

FIG. 5 illustrates a process flow 500 suitable for implementation by systems 200 or 400 of the present invention. In one aspect, it is recognized that data processing steps of the process flow 500 may be carried out via a pre-programmed algorithm executed by one or more processors of the one or more computing systems 242. Step 502 generates a beam of illumination. For instance, one or more laser sources may generate a beam of laser light. Step 504 directs a portion of the generated beam onto a surface of a spatial light modulator (SLM). For example, the beam splitter 204 of system 200 may act to direct at least one portion of the illumination beam 210 toward the SLM (e.g., diffractive-based SLM). Step 506 directs at least a portion of the generated beam incident on the surface of the SLM through an aperture of an aperture stop and onto one or more target structures of one or more samples. For example, the SLM 206 of system 200 may direct at least a portion of the illumination beam incident on the surface of the SLM through the aperture 219 and onto one or more targets 229 of the wafer 230. Step 508 generates a selected illumination pupil function of the illumination transmitted through the aperture utilizing the SLM in order to establish a contrast level of one or more field images of the one or more target structures above a selected contrast threshold. In this regard, the SLM 206 and the metrology tool 242 (both controlled by the computing system 242) may operate in a feedback mode in order to achieve an illumination pupil function suitable for producing a contrast level of one or more field images acquired using the metrology tool 242 above a selected contrast level. Alternatively, the SLM 206 and metrology tool 242 feedback mode may be utilized to achieve an optimal or near-optimal contrast level of one or more field images acquired using the metrology tool 242. Step 510 performs one or more metrology measurements on the one or more target structures (e.g., targets 229) utilizing the selected illumination pupil function. For example, the metrology tool 224 may be controlled by the one or more computing systems 242 such that upon achieving an optimal or near-optimal contrast level (via the selected illumination pupil function) the computing system 242 may direct the metrology tool 224 to perform overlay metrology measurements.

In a further embodiment of process 500, a first target structure may be measured at a first illumination function, while a second target structure is measured at a second illumination function that is different from the first illumination function. In this manner, the first illumination function may be matched to the first target structure utilizing the SLM and the second illumination function is matched to the second target structure utilizing the SLM. It should be recognized that this embodiment may be readily extended to numerous target structures and should not be interpreted to merely two target structures as described above. In this manner, multiple target sites on a wafer may be measured sequentially, or "on the fly," with each target site being measured utilizing a different illumination pupil function allowing for contrast optimization for each target.

In a further embodiment, the process 500 may include acquiring a first field image of a bottom layer of a target structure, the first image acquired at a high contrast level relative to a background contrast level; acquiring a second field image of a top layer of the target structure, the second image acquired at a contrast level above a selected contrast threshold; and generating a metrology measurement image of the target structure by combining the first field image and the second field image utilizing a double grab algorithm. In this manner, the system 200 (or system 400) may employ a "double grab" sequence. The double grab sequence may include acquiring two images of a single overlay target whereby a double grab imaging algorithm utilizes the information obtain from the two images to provide a combined image with an increased level of contrast. For example, the system 200 may acquire two field images of a target, a first image with the bottom layer having very high contrast compared to the background and a second image with the top layer having its contrast optimized or nearly optimized. The system 200 (via computing system 242) may then digitally combine these images using known double grab algorithms in order to achieve a final image having very high contrast for both layers.

Figure 6:
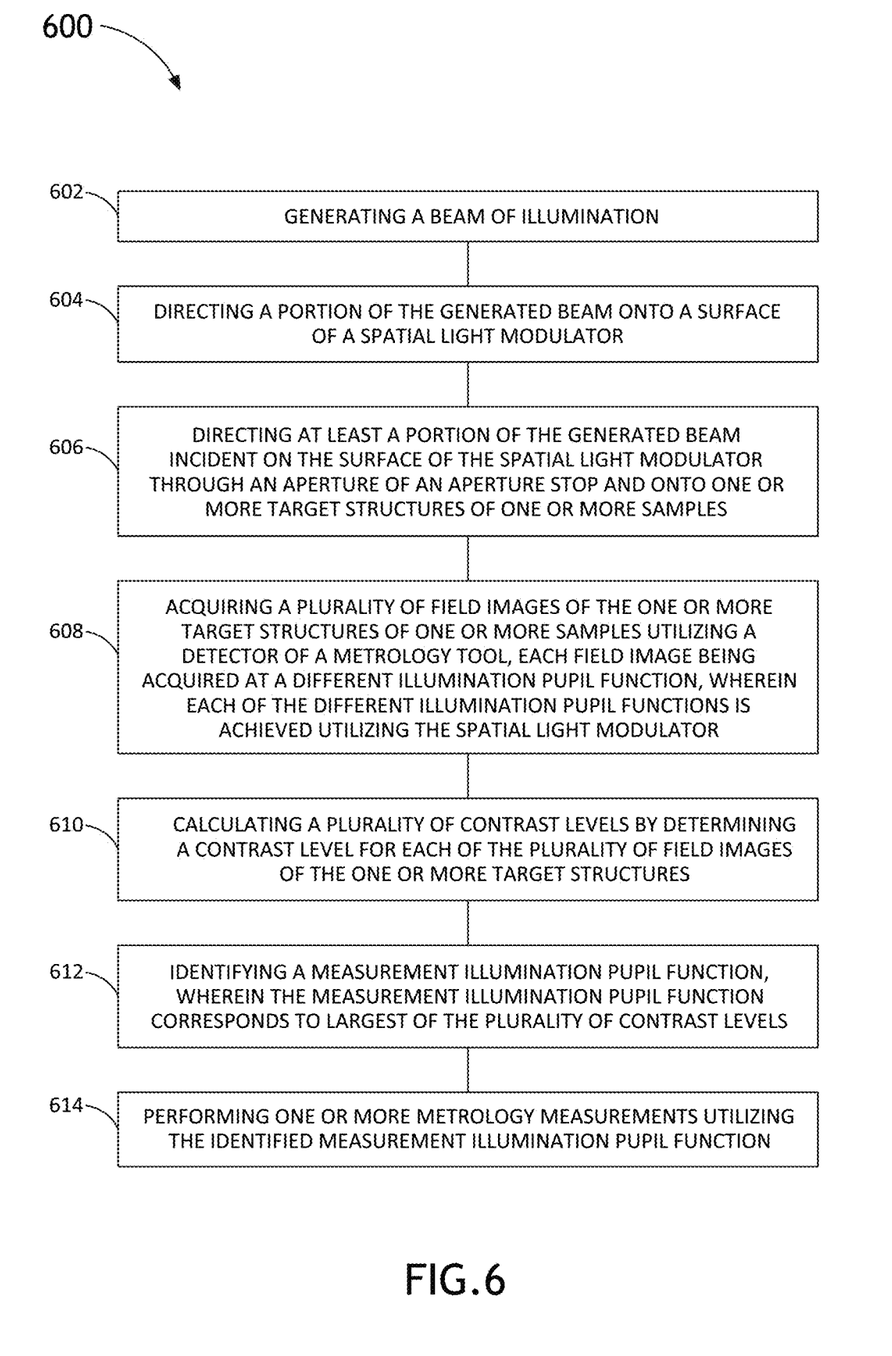
FIG. 6 is a process flow diagram of a method for contrast enhancement in a metrology tool, in accordance with one embodiment of the present invention.

FIG. 6 illustrates an alternative process flow 600 suitable for implementation by systems 200 or 400 of the present invention. Step 602 generates a beam of illumination. Step 604 directs a portion of the generated beam onto a surface of a spatial light modulator. Step 606 directs at least a portion of the generated beam incident on the surface of the spatial light modulator through an aperture of an aperture stop and onto one or more target structures of one or more samples. Steps 602, 604, and 606 are similar in nature to steps 502, 504, and 506 of process 500. Step 608 acquires a plurality of field images of one or more target structures (e.g., targets 229) of one or more samples utilizing a detector (e.g., CCD camera of a metrology tool, each field image being acquired at a different predetermined illumination pupil function, wherein each of the different illumination pupil functions is achieved utilizing the spatial light modulator (e.g., SLM 206). For example, a camera 240 of the metrology tool 224 may capture multiple field images of one or more targets 229, each field image being captured at a different illumination pupil function (i.e., illumination pupil configuration), the different illumination pupil functions established using the SLM 206 (e.g., diffractive SLM). Step 610 calculates a plurality of contrast levels by determining a contrast level for each of the plurality of field images of the one or more target structures. For example, the computing system 242 may receive the field images obtained at different illumination pupil functions from the camera 240. Upon receiving the digitized imagery data from the detector 240, the computing system 242 may then utilize one or more contrast metrics, as described previously herein, to calculate a contrast level for each of the acquired field images. Step 612 identifies a measurement illumination pupil function, wherein the measurement illumination pupil function corresponds to largest of the plurality of contrast levels. For example, the computing system 242 may then analyze and compare the set of calculated contrast levels associated with the multiple acquired field images of the targets 229 and identify the "measurement illumination pupil function," which corresponds to the illumination pupil function producing the highest contrast among the acquired field images. Step 614 performs one or more metrology measurements utilizing the identified measurement illumination pupil function. Step 614 is analogous to step 510 of process 500.

In one embodiment of process 600, the plurality of field images may be acquired over a plurality of focal planes. In another embodiment, the plurality of field images may be acquired over a range of one or more spectral parameters (e.g., wavelength) of the beam of illumination. In another embodiment, each of the plurality of field images may be acquired at a different target structure site (e.g., target 229 site) of the one or more samples (e.g., wafer 230). In another embodiment, the measurement illumination pupil function may be achieved by modifying a configuration of the SLM as function of wafer location or field location.

It should further be recognized that the limitations and embodiments described with respect to process flow 500 should be interpreted to extend to process flow 600 and vice versa. As such, the description above of process flow 500 and 600 should not be interpreted as a limitation but merely as illustrations.

All of the system and methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and/or firmware.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

Furthermore, it is to be understood that the invention is defined by the appended claims.

What is claimed:
1. An apparatus, comprising: an illumination source;
a spatial light modulator (SLM);
a beam splitter configured to direct a portion of light emanating from the illumination source along an illumination path to a surface of the spatial light modulator (SLM);
an aperture stop disposed substantially at a pupil plane of the illumination path, the aperture stop having an aperture configured to transmit at least a portion of light directed from the surface of the SLM to a surface of one or more specimens; and
a metrology tool configured to measure one or more characteristics of one or more metrology target structures of the one or more specimens, the metrology tool comprising:
an entrance pupil configured to receive illumination directed from the surface of the SLM and transmitted through the aperture of the aperture stop;
a beam splitter configured to receive illumination received through the entrance pupil of the metrology tool, the beam splitter further configured to direct at least a portion of the illumination passed through the entrance pupil to the one or more samples;
an objective lens configured to focus the at least a portion of the illumination onto one or more target structures of the one or more samples; and
a detector configured to collect a portion of illumination scattered from the one or more target structures of the one or more samples,
wherein the SLM is configured to control an illumination pupil function of the illumination transmitted through the aperture, the illumination pupil function controlled by controlling a profile of illumination impinging on the surface of the SLM from the illumination source.

2. The apparatus of claim 1, further comprising:
a computing system communicatively coupled to the detector of the metrology tool and configured to determine one or more overlay characteristics utilizing collected illumination data from the detector.

3. The apparatus of claim 1, further comprising:
a computing system communicatively coupled to the SLM and the detector of the metrology tool, the computing system configured to:
receive a plurality of field images of the one or more target structures from the detector, each of the field images acquired at a different illumination pupil function;
calculate a contrast level for each of the plurality of field images of the one or more target structures utilizing illumination collection data from the detector and one or more contrast metrics;
determine an illumination function suitable for producing a contrast level above a select contrast threshold utilizing the calculated contrast levels for each of the plurality of field images; and
control the SLM in response to the determined illumination pupil function in order to establish an illumination pupil function suitable for producing a contrast level above the selected contrast threshold.

4. The apparatus of claim 3, wherein the metrology tool is configured to perform one or more metrology measurements utilizing the determined illumination pupil function.

5. The apparatus of claim 1, wherein the spatial light modulator comprises:
a diffraction-based spatial light modulator.

6. The apparatus of claim 1, wherein the spatial light modulator comprises:
a reflection-based spatial light modulator.

7. The apparatus of claim 1, wherein the spatial light modulator comprises:

a microelectro-mechanical systems (MEMS) spatial light modulator.

8. The apparatus of claim 1, wherein the spatial light modulator comprises:
a liquid crystal spatial light modulator.

9. The apparatus of claim 1, wherein the illumination source comprises:
one or more lasers.

10. The apparatus of claim 1, wherein the one or more specimens comprise:
one or more semiconductor wafers.

11. The apparatus of claim 1, wherein the one or more target structures comprise:
at least one of one or more box-in-box (BiB) targets or one or more advanced imaging metrology (AIM) targets.

12. The apparatus of claim 1, wherein the detector comprises:
at least one of a charge-coupled device (CCD) camera or a time delay integration (TDI) camera.

13. An apparatus, comprising:
a laser light source configured to generate one or more laser beams;
an integration rod optically coupled to an output of the laser source; a micro mirror array (MMA) chip;
a beam splitter configured to direct a portion of light emanating from the integration rod along an optical path toward a surface of the MMA chip;
a set of optical relay optics configured to receive the directed portion of light from the beam splitter and relay the portion of light to the MMA chip;
a metrology tool configured to measure one or more characteristics of one or more metrology target structures of one or more samples, the metrology tool comprising:
an entrance pupil configured to receive illumination directed from the surface of the MMA chip;
a beam splitter configured to receive illumination received through the entrance pupil of the metrology tool, the beam splitter further configured to direct at least a portion of the illumination passed through the entrance pupil to the one or more samples;
an objective lens configured to focus the at least a portion of the illumination onto one or more target structures of the one or more samples; and
a detector configured to collect a portion of illumination scattered from the one or more target structures of the one or more samples,
a removable lens positioned along an imaging path of the metrology tool and configured to alternate the detector between imaging the one or more samples and a pupil of the objective, the MMA chip being imaged to the pupil of the objective,
wherein the MMA chip is configured to control a profile of illumination impinging on the surface of the MMA chip from the laser source.

14. The apparatus of claim 13, wherein the set of optical relay optics comprises:
a set of Schlieren optics.

15. The apparatus of claim 13, further comprising: a computing system communicatively coupled to the MMA chip and the detector of the metrology tool, the computing system configured to:
receive a plurality of field images of the one or more target structures from the detector, each of the field images acquired at a different illumination pupil function;
calculate a contrast level for each of the plurality of field images of the one or more target structures utilizing illumination collection data from the detector and one or more contrast metrics;
determine an illumination function suitable for producing a contrast level above a selected contrast threshold utilizing the calculated contrast levels of the plurality of field images; and
control the MMA chip in response to the determined illumination pupil function in order to achieve an illumination pupil function suitable for producing a contrast level above the selected contrast threshold.

16. The apparatus of claim 15, wherein the metrology tool is configured to perform one or more metrology measurements utilizing the determined illumination pupil function.

17. The apparatus of claim 13, wherein the one or more samples comprise:
one or more semiconductor wafers.

18. The apparatus of claim 13, wherein the detector comprises:
at least one of a charge-coupled device (CCD) camera or a time delay integration (TDI) camera.

19. A method, comprising: generating a beam of illumination;
directing a portion of the generated beam onto a surface of a spatial light modulator (SLM);
directing at least a portion of the generated beam incident on the surface of the SLM through an aperture of an aperture stop and onto one or more target structures of one or more samples;
generating one or more selected illumination pupil functions of the illumination transmitted through the aperture utilizing the SLM; and
performing one or more metrology measurements on the one or more target structures utilizing the selected illumination pupil function.

20. The method of claim 19, wherein the spatial light modulator comprises:
a diffraction-based spatial light modulator.

21. The method of claim 19, wherein a first target structure is measured at a first illumination function and at least a second target structure is measured at a second illumination function different from the first illumination function, wherein the first illumination function is matched to the first target structure utilizing the SLM and the second illumination function is matched to the at least a second target structure utilizing the SLM.

22. The method of claim 21, wherein the performing one or more metrology measurements on the one or more target structures utilizing the selected illumination pupil comprises:
acquiring a first field image of a bottom layer of a target, the first image acquired at a high contrast level relative to a background contrast level;
acquiring a second field image of a top layer of the target, the second image acquired at a contrast level above a selected contrast threshold; and
generating a metrology measurement image of the target by combining the first field image and the second field image.

23. A method, comprising: generating a beam of illumination;
directing a portion of the generated beam onto a surface of a spatial light modulator;
directing at least a portion of the generated beam incident on the surface of the spatial light modulator through an aperture of an aperture stop and onto one or more target structures of one or more samples; and acquiring a plurality of field images of the one or more target structures of one or more samples utilizing a detector of a metrology tool, each field image being acquired at a different illumination pupil function, wherein each of the different illumination pupil functions is achieved utilizing the spatial light modulator;

identifying a measurement illumination pupil function based on the plurality of the field images acquired at different illumination pupil functions; and performing one or more metrology measurements utilizing the identified measurement illumination pupil function.

24. The method of claim 23, wherein the spatial light modulator comprises:
a diffraction-based spatial light modulator.

25. The method of claim 23, wherein acquiring a plurality of field images of the one or more target structures comprises:

acquiring a plurality of field images of the one or more target structures over a plurality of focal planes.

26. The method of claim 23, wherein acquiring a plurality of field images of the one or more target structures comprises:

acquiring a plurality of field images of the one or more target structures over a range of one or more spectral parameters of the beam of illumination.

27. The method of claim 23, wherein acquiring a plurality of field images of the one or more target structures comprises:

acquiring a plurality of field images of the one or more target structures at one or more target structure sites of the one or more specimens.

28. The method of claim 23, wherein the measurement illumination pupil function is achieved by modifying a configuration of the SLM as function of at least one of wafer location or field location.

* * * * *